United States Patent [19]

Russell

[11] Patent Number: 5,012,116
[45] Date of Patent: Apr. 30, 1991

[54] SYSTEM FOR INSPECTING BEARING BALLS FOR DEFECTS

[76] Inventor: John P. Russell, 107 W. Richland St., Summerville, S.C. 29483

[21] Appl. No.: 422,102

[22] Filed: Oct. 12, 1989

[51] Int. Cl.$^5$ ............................................. G01N 21/88
[52] U.S. Cl. .................................... 250/572; 356/446
[58] Field of Search ............... 250/571, 572, 562, 563; 356/445, 446, 371, 430, 431, 237

[56] References Cited

U.S. PATENT DOCUMENTS

| 4,227,809 | 10/1980 | Satoh et al. | 356/446 |
| 4,259,013 | 3/1981 | Faxvog et al. | 356/237 |
| 4,555,635 | 11/1985 | Yoshida | 250/572 |

OTHER PUBLICATIONS

R. L. Lewis "Optical Scanners for Ball Bearing Inspection" Optical Engineering Jan./Feb. 1982, pp. 113–117.

Primary Examiner—David C. Nelms
Attorney, Agent, or Firm—George J. Seligsohn

[57] ABSTRACT

By deriving the image formed by light specularly-reflected from substantially all of the convex (mirror-like) spherical surface of a bearing ball under test that is being illuminated with diffuse light, any defect in the bearing ball under test reveals itself as a light-contrast pattern in the otherwise substantially uniform diffuse background of the image.

26 Claims, 5 Drawing Sheets

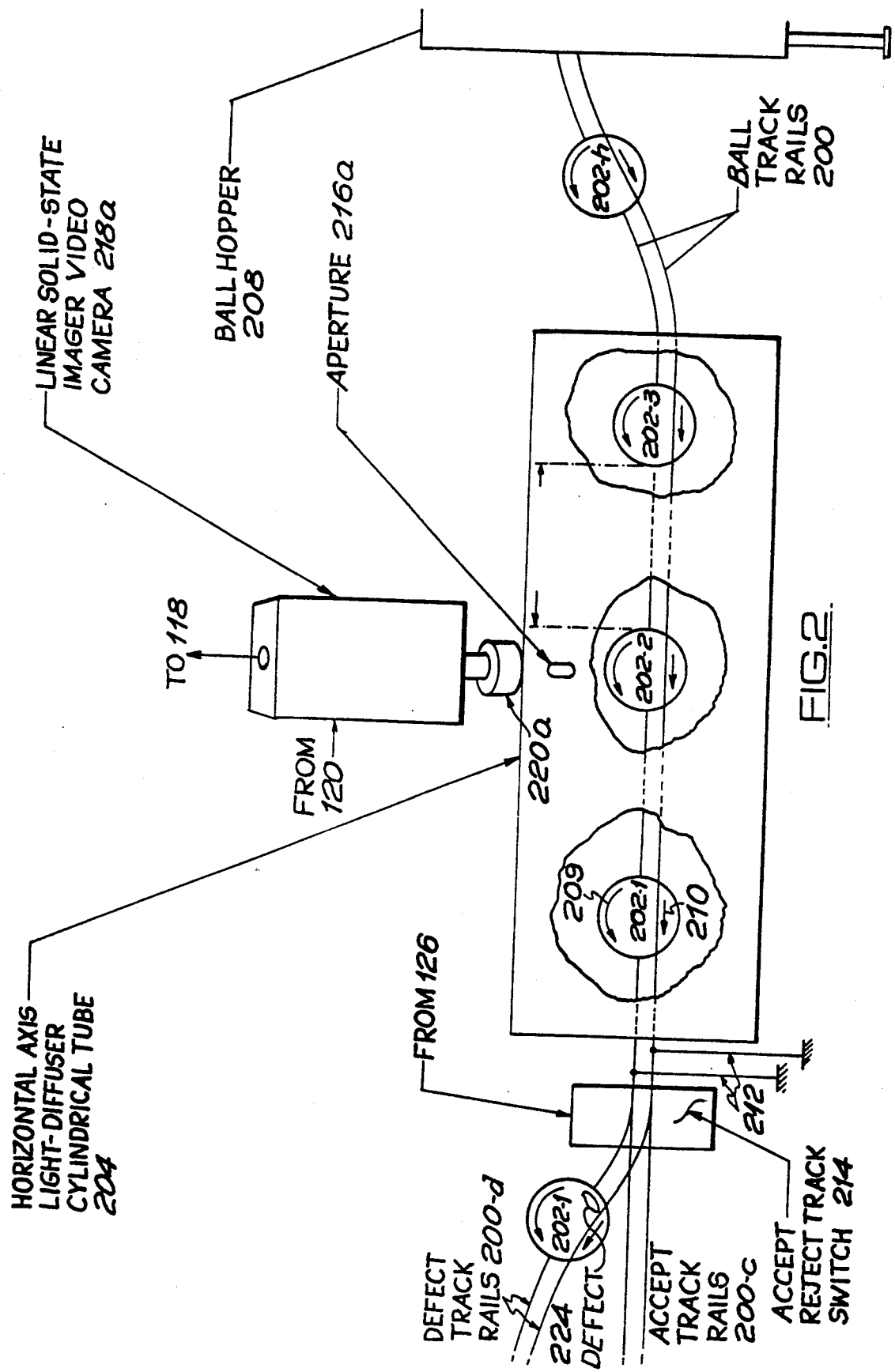

TIME=t₃
(STOP COUNTING CAMERA SCANS)

TIME=t₂
(STOP BALL INSPECTION)

TIME=t₁
(START BALL INSPECTION)

TIME=t₀
(START COUNTING CAMERA SCANS)

SYSTEM FOR INSPECTING BEARING BALLS FOR DEFECTS

BACKGROUND OF THE INVENTION

This invention relates to automatic systems for inspecting bearing balls and, more particularly, to opto-electronic systems for inspecting bearing balls which have a specularly-reflecting convex surface.

A defect in a bearing ball is likely to cause failure of a costly and complex device in which a ball bearing containing the defective ball is incorporated. For this reason, it is essential that each manufactured bearing ball be inspected for defects before being incorporated in a device. Defects include pits, burrs, scratches, scuffs and rust spots in the convex (spherical) surface thereof. In order to minimize friction, the spherical surface of a bearing ball is normally polished to a high degree so that the bearing ball surface operates as a convex mirror the specularly reflects incident light.

In the past, trained personnel visually inspected each manufactured bearing ball for defects in the surface thereof. This is relatively slow and, therefore, a relatively costly operation. Further, a small but still significant number of false positives (a defective bearing ball being found to be acceptable) occur with visual inspection.

More recently, automatic bearing ball inspection systems, including opto-electronic systems, have been developed for the purpose of increasing both the speed and reliability of inspection, thereby reducing the cost of inspection.

Prior-art opto-electronic bearing ball inspection systems illuminate each of one or more spots of the specularly-reflecting convex surface of a bearing ball under test with an incident beam of non-diffuse (e.g., "point source" light). One or more suitably placed light detectors receives light specularly-reflected from a corresponding one of the illuminated spots of the convex (spherical) surface of the bearing ball under test. Electronic means coupled to each of the light detectors measures the light intensity received thereby. A defect occurring at any illuminated spot of the bearing ball surface will scatter or absorb the incident light, rather than specularly-reflecting it. This will result in a modification of the light intensity received by at least one light detector. The electronic means, noting a modification in the light intensity, will indicate whether the bearing ball under test is defective, and preferably actuate accept-reject mechanical ball-separation means for removing the defective bearing ball under test.

In order to insure that substantially each and every spot on the entire spherical surface of the bearing ball under test is effectively illuminated by an incident light beam, the bearing ball under test is moved in a predetermined ordered manner with respect to both the incident light beam source or sources and the suitably-placed light detector or detectors. In accordance with one prior-art technique, the bearing ball under test is simultaneously rotated about each of two perpendicular axes at two appropriate different predetermined angular velocities by means of a suitable differential mechanism. In accordance with another prior-art technique, the bearing ball under test is rolled at a constant predetermined angular velocity down a pair of horizontal track rails. The two track rails are separated from one another by a distance which is only very slightly less than the diameter of the bearing ball under test. The result is that in rolling a full revolution, the bearing ball under test will translate horizontally on the track by a very small distance (i.e., the ratio of angular velocity to the translational velocity of the bearing ball under test is very large). The prior-art opto-electronic bearing ball inspection system employing the aforesaid second-mentioned technique for moving the bearing ball under test is stated to have a sensitivity sufficient to detect a defect having a dimension of 10 mils (0.01 inches) or larger.

SUMMARY OF THE INVENTION

The opto-electronic inspection system of the present invention illuminates the convex specularly-reflecting surface of a bearing ball under test with diffuse light, rather than the non-diffuse illuminating light employed by the prior art. Illumination of the specularly-reflecting surface of a non-defective bearing ball under test results in diffuse relatively high intensity (e.g., white) light being reflected therefrom. This is the same result that would be obtained if a ball, having a white spherical surface, were illuminated with non-diffuse light. In both cases, the reflected light would be diffuse. Any defect in the specularly-reflecting surface of a ball under test shows up as a light-contrast pattern delineated by a distinct boundary edge from a white background of reflected light. More specifically, the present invention is directed to a system for inspecting a bearing ball for the presence of a defect in the normally specularly-reflecting convex surface thereof. The system comprises first means for illuminating the surface with diffuse light thereby to reflect a light-contrast pattern of a defect, if present, with respect to a diffuse light background reflected from the normally specularly-reflecting convex surface. The system also comprises second means including light imaging means responsive to light reflected from substantially all points of the convex surface for detecting the presence of the light-contrast pattern.

BRIEF DESCRIPTION OF THE DRAWING

FIGS. 2, 2a and 2b diagrammatically illustrate a preferred embodiment of the present invention that is functionally shown in FIG. 1;

DESCRIPTION OF THE PREFERRED EMBODIMENTS

Figure 1:
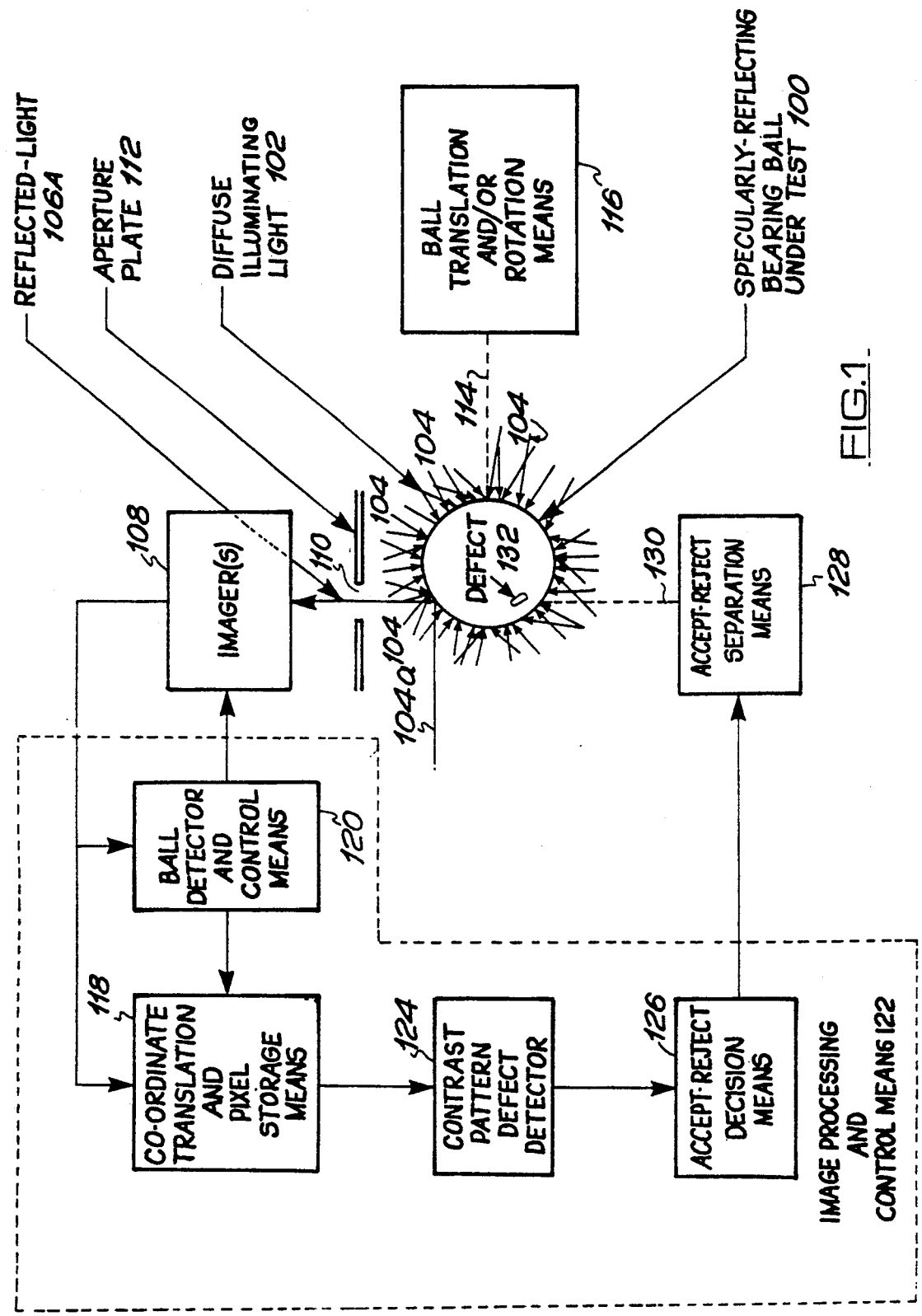
FIG. 1 is a functional block diagram illustrating the basic principles of the present invention.

FIG. 1, which is a functional block diagram illustrating the basic principles of the present invention, may be implemented in various ways. The specific way in which many of the functions shown in FIG. 1 are performed may vary depending on the particular implementation.

As shown in FIG. 1, the spherical convex surface of illuminated by diffuse illuminating light 102 from a diffuse light source (not shown in FIG. 1). As indicated by arrows 104, the diffuse light arriving at many different angles of incidence illuminates each point of the specularly-reflecting bearing ball under test 100. Like all specularly-reflecting surfaces, each incident ray 104 of light arriving at a point of the surface of bearing ball under test 100 gives rise to a corresponding reflected ray from that point which has an angle of reflection equal to the angle of incidence (such as reflected-light ray 106a having an angle of reflection equal to its angle of incidence of incident-light ray 104a).

Depending upon the particular implementation of FIG. 1, block 108 represents either a single imager or a plurality of imagers angularly spaced about bearing ball under test 100. Further, depending upon the particular implementation, each imager may be a simple light detector comprised of a single photocell or may be a video camera comprised of a one or two dimensional array of photocells (preferably a solid-state array that is periodically scanned). Each imager receives a narrow beam of reflected rays (such as reflected-light ray 106a) from the surface of bearing ball under test 100 that has passed through a small aperture 110 in an aperture plate 112. Aperture plate 112 substantially prevents any of diffuse illuminating light 102 from reaching the imager 108.

Bearing ball under test 100 is mechanically coupled (indicated by dashed line 114) to ball-translation and/or rotation means 116. Depending upon the particular implementation of FIG. 1, means 116 may simultaneously translate bearing ball under test 100 in one direction at a given linear velocity by rotating bearing ball under test 100 at a given angular velocity about an axis perpendicular to this one direction (as is known in the prior art). Alternatively, means 116 may simultaneously rotate bearing ball under test 100 at a first angular velocity about a first axis, while rotating bearing ball under test 100 at a second given velocity about a second axis perpendicular to the first axis (as is also known in the prior art).

Regardless of the particular implementation of FIG. 1, the movement of bearing ball under test 100 by means 116 together with the scanning of imagers 108 (in the case in which the imager or imagers 108 happen to be one or more video cameras) is such that reflected light rays, such as reflected-light ray 106a, is received from substantially every point of the surface of bearing ball under test 100 by an imager of imager or imagers 108 during a given time cycle.

Respective outputs of the one or more imagers 108 are applied as inputs to coordinate translation and pixel storage means 118 and ball-detector and control means 120 of image processing and control means 122 normally comprises digital processing having digital computing capabilities. In this case, the image information originally received by the one or more imagers 108 in analog form is converted to digital form by one or more analog-to digital converters that may be located either in each of the imagers 108 or, alternatively, may be located in image processing and control means 122.

As indicated in FIG. 1, ball-detector and control means 120 includes a first output that is applied as an input to each of the one or more imagers 108 and a second output that is applied as an input to coordinate translation and pixel storage means 118. The output from coordinate translation and pixel storage means 118 is applied as an input to contrast-pattern defect detector 124. The output from contrast-pattern defect detector 124 is applied as an input to accept-reject decision means 126. The output from accept-reject decision means 126, which constitutes the output from image processing and control means 122, is applied as an input to accept-reject separation means 128. Accept-reject separation means 128, which is a mechanical means whose operation is controlled by the output from accept-reject decision means 126, is mechanically coupled (as indicated by dashed line 130) to bearing ball under test 100 for separating defective bearing balls from nondefective bearing balls.

The operation of the bearing ball inspection system shown in FIG. 1 will now be considered. It is apparent that in the absence of a bearing ball under test from the field-of-view of any of the one or more imagers 108, the signal intensity of the output from all of the one or more imagers 108 will be low, since substantially no reflected light reaches any of the one or more imagers 108 in this case. Therefore, the ball detector of means 120 can detect the presence of a bearing ball under test coming into view of at least one of the one or more imagers 108 by the signal strength of the output from at least one of the one or more imagers 108, applied as an input to the detector ball, changing from a low intensity to a relatively high intensity.

The detection of the bearing ball under test coming into view by the ball detector of means 120 initiates a timing cycle by timing means included within ball detector and control means 120. The inspection of the bearing ball under test 100 takes place during this timing cycle, but the inspection period does not necessarily start at the beginning of the timing cycle. The timing means may provide a certain delay between the beginning of the timing cycle and the beginning of an inspection period. Further, the timing means may terminate the inspection period before the end of the timing cycle. Just where the inspection period begins and ends with respect to the beginning and end of the timing cycle depends upon the particular implementation of FIG. 1. However, in any case, the entire surface of the specularly-reflecting bearing ball under test 100 should be inspected in a predetermined and orderly manner during the inspection period portion of the timing cycle.

If the one or more imagers 108 are comprised of scanning video cameras, rather than simple light detectors, the timing means of detector ball and control means 120 provides periodic sync signals at the proper frequency to control the scan of the one or more videocamera imagers. Further, during the inspection period of the timing cycle, the timing means of detector ball and control means 120 applies timing signals to coordinate translation and pixel storage means 118 to the signal stream from the one or more imagers 108 which are applied as respective inputs to coordinate translation and pixel and storage means 118.

The stream of pixels from the one or more imagers 108 during an entire inspection period represents an image of the entire specularly-reflecting spherical surface of the bearing ball under test 100. It is desired to store this image as a flat two-dimensional spherical surface of the bearing ball under test 100, rather than as a spherical (globe-type) map. In order to accomplish this, it is necessary to convert from spherical coordinates to Cartesian (or polar) coordinates.

This is accomplished by the coordinate translation portion of means 118, taking into consideration the predetermined and ordered inspection of the respective points of the specularly-reflecting spherical surface of the bearing ball under test 100 as well as any image distortion that is known to take place in the imaging of the respective pixels by the one or more imagers 108. Under the control of the timing signals applied thereto from means 120, means 118 stores each of the coordinate-translated pixels derived thereby in an appropriately addressed memory location of the pixel storage means thereof. The result is that a two-dimensional planar map (preferably in Cartesian coordinates) of the specularly-reflected image of the spherical surface of bearing ball under test 100 is stored in the pixel storage portion of means 118.

If one were to display a frozen frame of the image stored in the pixel storage portion of means 118 on a video monitor, and if the bearing ball under test 100 were non-defective, the display on the video monitor would be a white image, which if not of uniform brightness, would change in brightness only slightly and very gradually over the entire area of the display. The reason for this is that the specularly-reflecting spherical surface of bearing ball under test 100 operates as convex mirror that reflects an image of the diffuse light, and it is this diffuse-light image that is displayed by a monitor responsive to the stored information in means 118. The appearance of such a display would be similar to that observed in looking at a cloud.

If bearing ball under test 100 contains a defect, such as defect 132, and the defect is in the form of a pit, burr, scratch or rust spot, incident light thereon would be scattered or absorbed therefrom, rather than being specularly reflected. On the other hand, a defect such as a scuff concentrates the light reflected from a specularly-reflecting convex surface. The result is that the display on a monitor of the image stored in means 118 derived from a defective bearing ball under test would exhibit a light-contrast pattern of the defect with respect to the white background of the non-defective portion of the bearing ball under test. In the case of a scuff defect, the concentration of the reflected light would result in the contrast pattern being brighter than the background, while the other types of defects, which cause scattering or absorption of the reflected light, result in the contrast pattern being darker than the background. In all cases, however, the defect contrast pattern is delineated from the background by a distinct boundary edge.

Since normally there is no need for the reflected image of the bearing ball under test to be visually displayed, FIG. 1 does not include a monitor. However, there are special situations, such as reinspecting each of a group of bearing balls that have been previously found to be defective during an original inspection, in which it may be desirable to visually observe the type of defect on each bearing ball on a monitor display. Thus, it is in the contemplation of the present invention to display the reflected image stored in the pixel storage portion of means 118 on a video monitor.

Contrast-pattern defect detector 124, which may include horizontal and vertical edge-detector digital filters, operates on the stream of reflected-image pixels read out of storage from means 118. More specifically, detector 124 derives an output signal indicative of the occurrence and distribution of significant changes in pixel signal level, if any. Accept/reject decision means 126, at the very least, responds to the output signal from detector 124 applied as an input thereto in deriving an "accept" output signal state in response to the complete absence of any contrast pattern (i.e., zero significant changes in pixel signal level). Otherwise, means 126 derives a "reject" output signal state. A more sophisticated accept/reject decision means 126 could derive a plurality of "reject" signal states for the purpose of categorizing reject-indicating contrast patterns by size and shape in accordance with the distribution of significant changes in pixel signal level.

Accept-reject separation means 130, which may include one or more switches, mechanically forwards bearing balls found to be non-defective (i.e., acceptable) along a first path and forwards bearing balls found to be defective (i.e., a reject) along a second path (or if the defective bearing balls have been categorized by size and/or shape, along an appropriate one of a plurality of second paths).

In order to be fail-safe, it is desirable that in the absence of any signal input to separation means 128, separation means 128 always operates to reject the bearing ball under test.

Figure 2A:
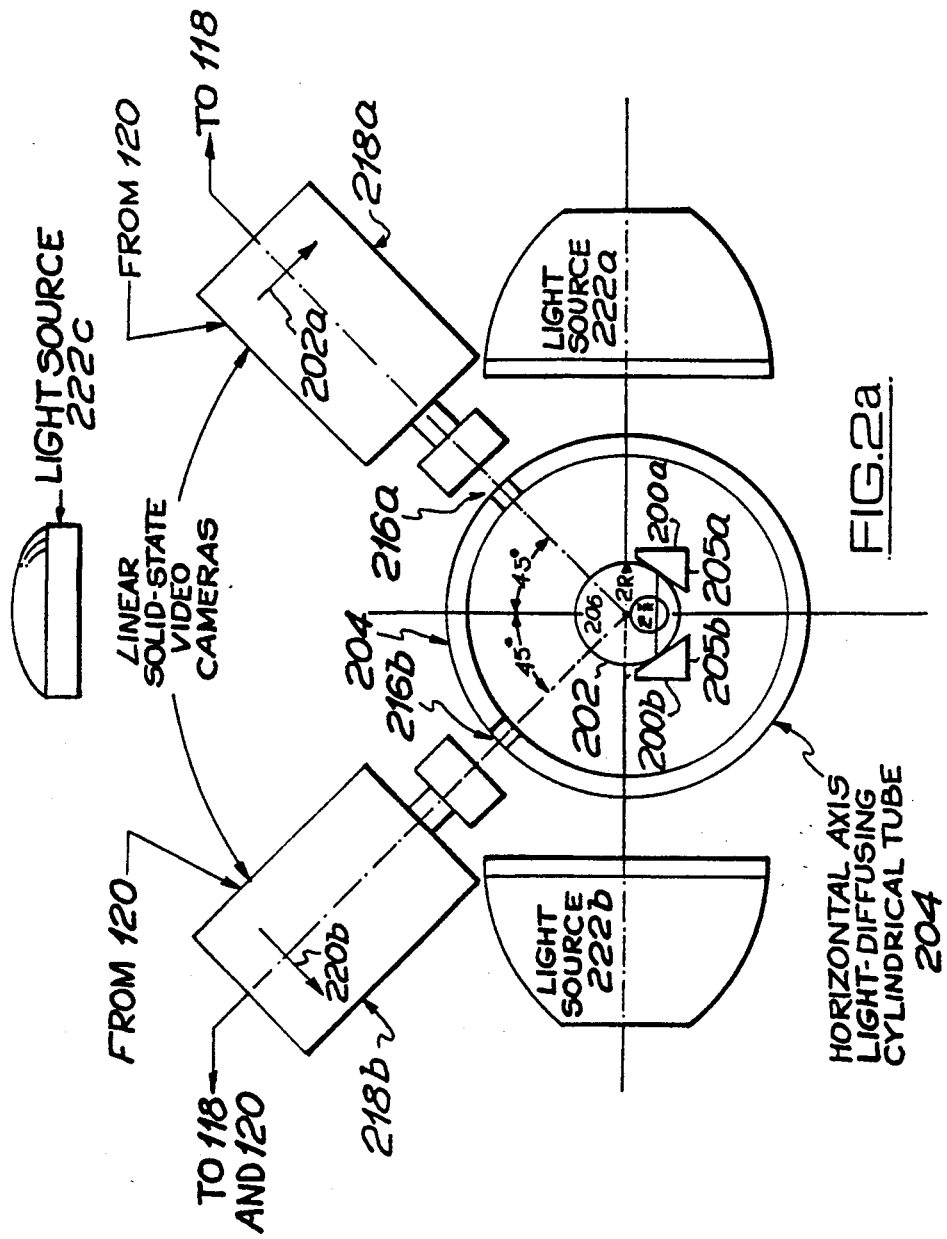
Figure 2B:
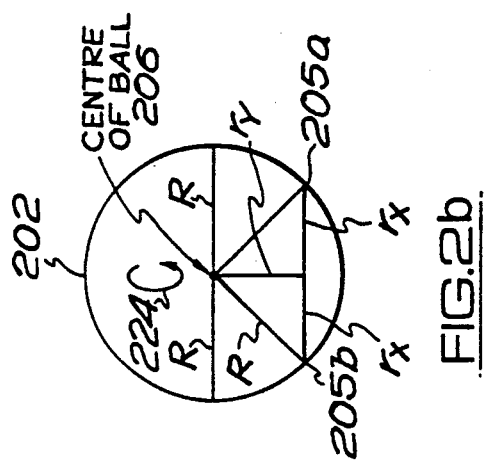
Figure 3D:
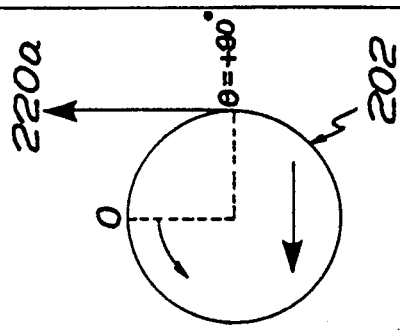
FIGS. 3a, 3b, 3c and 3d are timing diagrams helpful in understanding the operation of the preferred embodiment of the present invention shown in FIG. 2.
Figure 3C:
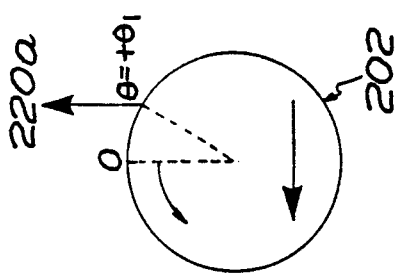
Figure 3B:
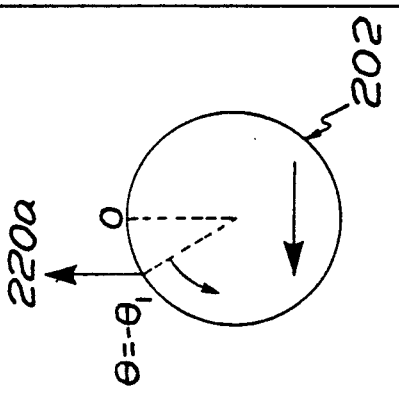
Figure 3A:
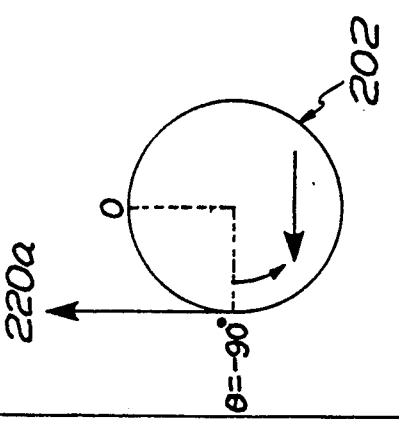

What is believed to be the most practical implementation of the bearing ball inspection system of FIG. 1 will now be described. As shown in FIG. 2, a horizontal portion of a pair of ball-track rails 200, which support a plurality of spaced bearing balls (e.g., bearing balls 202-1, 202-2 and 202-3), extends the entire length of horizontal-axis, light-diffusing cylindrical tube 204 that surrounds track rails 200. As made clear in FIG. 2a, the two track rails 200a and 200b, each of which has a tapered interior side, are separated from one another by a given amount which permits the two track rails 200a and 200b to support bearing ball 202 at points of contact situated below the horizontal diameter of bearing ball 202. Thus, as shown in FIG. 2a, the distance $2r_x$ between points of contact of bearing ball 202 with rails 200a and 200b is smaller than the diameter 2R of bearing ball 202. Further, as shown in FIG. 2a, the center of 206 of a bearing ball 202 is located substantially on the horizontal axis of light-diffusing cylindrical tube 204. FIG. 2b shows the geometric relationship among the horizontal latitudinal radius $r_x$ the distance $r_y$ of the latitudinal diameter $2r_x$ from the horizontal diameter of 2R of bearing ball 202, and the radius R of bearing ball 202.

Returning to FIG. 2, cylindrical tube 204 is relatively long with respect to its diameter (having a length-to-diameter ratio of about 6 to 1, by way of example). Ball-track rails 200, extending to the right of the right end of cylindrical tube 204, rise upward to near the top of free-standing ball-hopper 208. Ball-hopper 208 mechanically supports the right end of ball-track rails 200. Ball-hopper 208 contains mechanical means for periodically depositing a bearing ball 202 at the top of ball-track rails 200. A deposited bearing ball 202 rolls down ball-track rails 200 from ball-hopper 208 to the horizontal portion of ball-track rails 200. In rolling down from ball-hopper 208 to the horizontal portion of ball-track rails 200, a bearing ball is accelerated to a certain angular velocity and a certain linear velocity determined by the vertical distance through which the bearing ball has dropped. The bearing ball then continues to roll horizontally through the entire length of horizontal axis light-diffusing cylindrical tube 204. Since the friction between the points of contact of bearing ball and the ball-track rails is negligible, both the angular velocity and the linear velocity of a ball rolling the entire length of cylindrical tube 104 remains substantially constant at the certain angular velocity and certain linear velocity it achieved upon entering cylindrical tube 204 at the right end thereof. The spacing between two adjacent bearing balls rolling from right-to-left through cylindrical tube 204 depends both on the timing period of ball-hopper 208 in depositing successive bearing balls on ball-track rails 200 and the constant linear velocity of the bearing balls rolling on the horizontal portion of ball-track rails 200. Preferably, the timing period of ball-hopper 208 should be adjusted so that the spacing distance between two adjacent bearing balls rolling on the horizontal portion of ball-track rails 200 is substantially equal to the diameter of a bearing ball. The result is that shown in FIG. 2, in which the bearing ball 202-1 represents the earliest released bearing ball from ball-hopper 208 and respective bearing balls 202-2, 202-3 . . . 202-n represent successively later released bearing balls from ball hopper 208. The fact that each of bearing balls 202-1 . . . 202-n is simultaneously both being rolled and translated in a direction from right-to-left is schematically illustrated by respective arrows such as rolling arrow 209 and translation arrow 210 of bearing ball 202-1.

As schematically indicated in FIG. 2, ball-track rails 200 are ground supported at points beyond the left end of cylindrical tube 204 by support elements 212.

Further, at a point beyond the left end of cylindrical tube 204, ball-track rails 200 split into accept track rails 200c and defect track rails 200d. An accept-reject track switch 214 (corresponding to a species of accept-reject separation means 128 of FIG. 1) determines (in accordance with the output signal from accept-reject decision means 126 of FIG. 1) which one of accept track rails 200c or defect rails 200d a bearing ball exiting from the left end of cylindrical tube 204 will take.

As shown in FIGS. 2 and 2a, light-diffusing cylindrical tube 204 incorporates two small apertures 216a and 216b therein. In the axial direction of cylindrical tube 204, both apertures 216a and 216b are located substantially one-half way between the left and right opposite ends of cylindrical tube 204. In the circumferential direction of cylindrical tube 204, aperture 216a is situated substantially 45° from the top of cylindrical tube 204, as viewed in FIG. 2. Aperture 216b is situated 45° from the top of cylindrical tube 204 that is not viewable in FIG. 2. A first linear solid-state imager video camera 218a (shown in both FIGS. 2 and 2a) is situated in cooperative relationship with aperture 216a to receive reflected rays (such as ray 220a) of diffuse light from the specularly-reflecting surface of a bearing ball (such as bearing ball 202-2) rolling by aperture 216a. In a similar manner, second linear solid-state imager video camera 218b (shown only in FIG. 2a) is situated in cooperative relationship with aperture 216b to receive reflected rays of diffuse light from the specularly-reflecting surface of the bearing ball rolling by aperture 216b. Each of video cameras 218a and 218b, which receive scan sync signals from means 120 of FIG. 1, contains a solid state imager comprised of a linear array of photocells (e.g., a CCD linear imager). The linear imager of video camera 218a is oriented as shown by arrow 220a in FIG. 2a to image during each scan period a different slice of the upper right-hand quadrant of the spherical surface of bearing ball 202 then passing by aperture 216a. In a similar manner, the linear array of video camera 218b is oriented as shown by arrow 220b of FIG. 2a to image during each linear scan period a different slice of the upper-left hand quadrant of the spherical surface of bearing ball 202 then passing by aperture 216b.

Shown in FIG. 2a (but for clarity's sake not shown FIG. 2) are light sources 222a, 222b and 222c for illuminating from the outside light-diffusing cylindrical tube 204. Light from light sources 222a and 222b, in passing through light-diffusing cylindrical tube 204 to the interior thereof is substantially thoroughly diffused over the length of tube 204. Light sources 222a, 222b and 222c do not extend beyond the left and right ends of cylindrical tube 204. Therefore, the light intensity of any light entering either the left or right open end of cylindrical tube 204 is relatively small and is not diffuse.

The operation of the preferred embodiment of the bearing ball inspection system of the present invention shown in FIGS. 2, 2a and 2b will now be described. It is apparent from FIG. 2b that the rotation of bearing ball 202 in the direction shown by arrow 224 (i.e., out of the paper) through one complete revolution will result in bearing ball 202 being translated in a direction out of the paper by a distance equal to $2\pi r_y$. If instead of being rotated through one complete revolution of 360°, bearing ball 202 is only rotated through a fraction of a complete revolution, the translation distance is defined by the following equation:

$$\text{Translation distance} = [(360° - 2\theta)/360°][2\pi r_y] \quad (1)$$

Thus, for any given value of the angle $\theta$, the translation distance depends solely on the value $r_y$. However, as can be seen from FIG. 2b, the value of $r_y$ depends upon the value of $r_x$ in accordance to the following equation:

$$r_y = (R^2 - r_x^2)^{\frac{1}{2}} \quad (2)$$

Since the value of R, the radius of a bearing ball, is a constant for any given size bearing ball, the value $r_y$ can be controllably varied by appropriately changing the separation distance $r_x$ between track rails 200a and 200b (See FIG. 2a).

For reasons to be discussed in more detail below, it is desired that the translation distance be $2\sin\theta$. Substituting this value for translation distance and solving equation 1 for ry, results in the following:

$$r_y = [180°/(180° - \theta)][\sin\theta/\pi]R \quad (3)$$

FIGS. 3a, 3b, 3c and 3d show rolling and translating bearing ball 202 under test at each of four successive times $t_0$, $t_1$, $t_2$, and $t_3$, respectively. At time $t_0$, the bearing ball under test, in rolling from right-to-left, has just reached a position at which diffuse light reflected therefrom includes the reflected ray 220a that passes through aperture 216a and reaches video camera 218a. This results in the camera-output intensity applied to means 120 being sufficient for the ball detector thereof to determine that a bearing ball under test has just come into view of camera 218a. In response thereto, means 120 starts counting the number of camera scans. At time $t_1$, when means 120 has computed a first predetermined number of camera scans (this first predetermined number being related to the known constant horizontal translational velocity of rolling bearing ball 202 under test), bearing ball 202 under test has moved to the left by an amount such that, at time $t_1$, diffuse reflected light ray 220a that reaches camera 218a is reflected from a point on the spherical surface that is $\theta_1$ degrees to the left of the top of the rolling bearing ball 202 under test. At time $t_1$, in response to the camera-scan count reaching the first predetermined number, means 120 sends a control signal to means 118 that initiated the start of the ball inspection portion of the timing cycle that extends from $t_0$ to $t_3$. Control means 120 continues to count camera scans until the camera-scan count reaches a second predetermined number at time $t_3$. By time $t_2$, bearing ball under test 202 has moved further to the left so that now the diffuse reflected light ray 220a that reaches camera 218a is reflected from a point of the spherical surface of bearing ball 202 under test which is located at an angle of $\theta_1$ to the right of the top of bearing ball 202 under test at time $t_2$. Upon the camera-scan count reaching this second predetermined number, means 120 applies a control signal to means 118 to stop the ball inspection portion of the timing cycle. The timing could possibly end at time $t_2$. However, it is desirable to continue counting camera scans until the intensity of the output signal from camera 218a applied to the ball detector becomes low, which occurs at time $t_3$, when ball under test 202 has moved so far to the left that it leaves the field-of-view of camera 218a. By ending the timing cycle at time $t_3$, the constant linear horizontal velocity of the ball under test 202 may be accurately computed, since both the diameter of the ball under test and the camera-scan period are known. In this manner, any slight changes in the assumed constant linear horizontal translational velocity of the rolling balls under test can be continually corrected immediately after the inspection of each successive bearing ball.

It is intended that at least substantially every point in the front hemisphere of each bearing ball under test 202 be observed by video camera 218a during its passage from right-to-left through the entire field-of-view of video camera 218a (while simultaneously video camera 218b is observing at least substantially every point of the back hemisphere of this bearing ball under test 202). In the timing interval between time $t_3$, shown in FIG. 3b, and time $t_3$, shown in FIG. 3c, during which the entire bearing ball under test inspection takes place, the bearing ball under test undergoes a translation in position of $2\sin\theta_1$ (as is apparent from FIGS. 3b and 3c). In order that all points in the front hemisphere of the ball under test be observed by video camera 218a during the time interval between $t_1$ and $t_2$, it is necessary that the ball under test 202 roll through an angle of $360° - 2\theta_1$ during this time interval.

By substituting any desired particular value of $\theta_1$ for $\theta$ in equation 3, set forth above, a value for $r_y$ may be derived which will insure that all points on the front hemisphere of the bearing ball under test are observed by camera 118a. Once the proper value of $r_y$ has been derived, equation 2, set forth above, may be utilized to determine the proper spacing distance between the two ball-track rails 200 (i.e., $2r_x$) to achieve the desired value of $r_y$.

Figure 4:
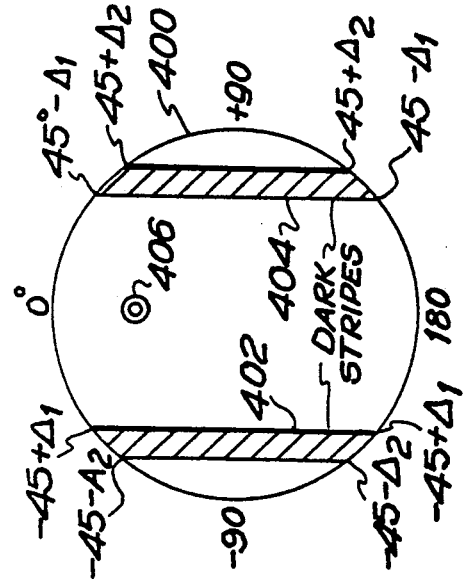
FIG. 4 diagrammatically illustrates the relative light intensity of imaged reflected light over the surface area of the bearing ball under test in the case of the preferred embodiment of the present invention shown in FIG. 2.

Now referring to FIG. 4, there is shown the reflected image of a bearing ball that would be received if the absolute value of $\theta_1$ (FIGS. 3b and 3c) were 90° (i.e., the ball-inspection time interval $t_2 - t_1$ were equal to the entire timing cycle period $t_3 - t_2$). In this case, as shown in FIG. 4, the reflected image 400 of a bearing ball will include two dark stripes 402 and 404 in the vicinity of $-45°$ latitude and $+45°$ latitude, respectively. More specifically, the width of dark stripe 402 extends from the $(-45 + \Delta_1)$ degree latitude to the $(-45 - \Delta_2)$ degree latitude and the width of dark stripe 404 extends from the $(45 - \Delta_1)$ degree latitude to the $(45 + \Delta_2)$ degree latitude. The cause of dark stripes 402 and 404 is that a bearing ball under test 202 is not illuminated by paraxial incident light rays due to the fact that both the left and right ends of light-diffusing cylindrical tube 204 are open. As the ratio of length-to-diameter of diffusing cylindrical tube 204 becomes larger, the respective values of both $\Delta_1$ and $\Delta_2$ (and, hence, the width of dark stripes 402 and 404) become smaller. As the ratio of the diameter of a bearing ball under test 202 to the diameter of the light-diffusing cylindrical tube 204 becomes larger, the ratio of $\Delta_1$ to $\Delta_2$ becomes smaller. Further, in actuality dark stripes 402 and 404 do not have the sharp edges in relative light intensity, shown in FIG. 4, but have blurred edges. In order to avoid all effects of dark stripes 402 and 404 and to insure that the light intensity of the reflected image 400 varies only slightly and gradually over its entire area, the angle $\theta_1$ should be selected to have a relatively small value (e.g., no larger than 36° and preferably about 30°). It will be seen from FIGS. 3b and 3c that in rolling from the position $-\theta_1$ to the position $+\theta_1$, bearing ball 202 is translated through a distance equal to $2\sin\theta_1$. Substituting $2\sin\theta_1$ for the translation distance in equation 1, and solving for the radius for $r_y$ in FIG. 2b, results in equation 3 (with the value $\theta_1$ being substituted for $\theta$). For instance, if $\theta_1$ is equal to 30°, the value of $r_y$ is equal to 0.191R, while the distance $2r_x$ between rails 200 is about 1.963R.

From the foregoing discussion, it would appear that by confining the absolute value of $\theta_1$ to a relatively small angle, such as 30°, an entirely white diffuse reflected image 400, without the spurious contrast patterns, such as dark stripes 402 and 404, would result from the inspection of a non-defective bearing ball under test 202. However, one problem remains. The fact is that during the inspection of a bearing ball 202, when the value of $\theta$ is in the vicinity of zero degrees, the aperture opening 216a and 216b will have an effect similar to that of left and right end openings of cylindrical tube 204, described above. The left and right end openings of cylinder 204 result in dark stripes 402 and 404 in the vicinity of $+45$ degrees. In the case of apertures 216a situated in the vicinity of zero degrees in which both the angle of incidence and the angle of reflection approach zero, the incident light ray coincides substantially with the reflected light ray, such as reflected light ray 220a, emerging through aperture 216a (i.e., the reflected light ray is retroreflected). However, due to the opening of aperture 216a, there is no incident light illuminating bearing ball under test 202-2 at substantially this zero angle of incidence. The result is a small blind spot 406 at the zero degree latitude (and 45° longitude) due to aperture 216a. A similar blind spot at zero degree latitude (and 135° longitude) results from aperture 216b.

From a statistical point of view, the chance that a bearing ball under test would contain only a single defect, and a single defect that is so positioned at the zero degree latitude that it coincides with blind spot 406 and is so small that it is entirely confined to the area of small blind spot 406, is highly unlikely (but not impossible). Therefore, one may be prepared to take this slight risk. However, the use of auxiliary means, such as shown in FIG. 5a or 5b, completely solves the problem of blind spot 406.

Figure 5B:
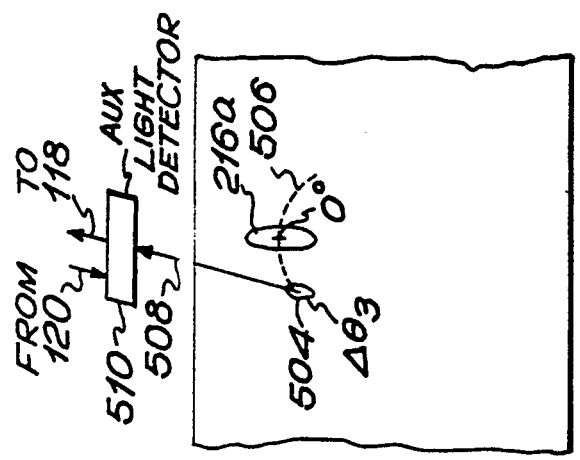
FIGS. 5a and 5b illustrate, respectively, alternative embodiments of auxiliary apparatus that is preferably added to the preferred embodiment shown in FIG. 2.
Figure 5A:
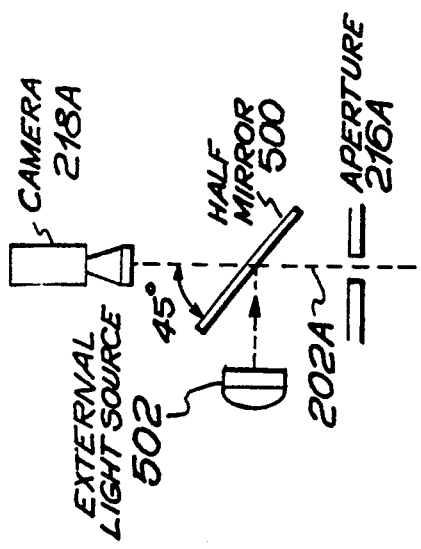

Referring to FIG. 5a, there is shown half-mirror 500 situated outside of light-diffusing cylindrical tube 204 and located in between aperture 216a and video camera 218a. Half-mirror 500 is oriented at a 45° angle with respect to reflected ray 220a. Light from external light source 502, which is controlled by control means 120 only during the middle of the timing cycle when $\theta$ has a value of substantially zero degrees (i.e., when retroreflection takes place through aperture 216a). The portion of a retroreflected light, which includes reflected ray 220a, is transmitted through half-mirror 500 and is received by video camera 218a. The only disadvantage of employing the auxiliary means shown in FIG. 5a is that the relative light intensity received by video camera 218a is reduced by the presence of half-mirror 500. The auxiliary means shown in FIG. 5b does not suffer from this disadvantage.

Referring to FIG. 5b, there is shown an auxiliary aperture 504 in cylindrical tube 204. Auxiliary aperture 504 is situated in cooperative spatial relationship with the path 506 that the 45° longitude takes as bearing ball under test 202 rolls from right to left through the given small angle $\Delta\theta_3$. The result is that the area of the rolling ball constituting the blind spot through aperture 216a at its zero degree latitude position, will be situated in cooperative relationship with auxiliary aperture 504 a short time later when bearing ball under test 202 has rolled downstream through an angle of $\Delta\theta_3$. At $\Delta\theta_3$, the formerly blind spot area is illuminated by diffuse light to provide a reflected ray 508 oriented normal to the axis of cylindrical tube 204. Reflected ray 508 is received by auxiliary light detector 510, which may be a simple light detector rather than a video camera. Light detector 510 is normally disabled, but is enabled by means 120 at the time during the timing cycle at which the blind spot area of bearing ball under test 202 is in the immediate vicinity of aperture 504. The output signal from detector 510, indicative of the light intensity of reflected ray 508, is applied to means 118, which interprets the respective spatial location thereof as though it occurred in the vicinity of the zero degree latitude and 45° longitude of the ball under test 202.

It should be understood that the auxiliary means of FIG. 5b could be situated upstream from the zero degree latitude position, rather than downstream. Further, rather than employing a simple auxiliary light detector, the approach employed in FIG. 5b in solving the blind spot problem could be implemented with an entire redundant video camera system situated either downstream or upstream from the zero degree latitude position of the bearing ball under test 202. It should also be understood that a duplicate auxiliary means of either FIG. 5a or 5b is employed in connection with aperture 216b.

Returning now to FIG. 2, the linear solid state imager employed in either video camera 218a or 218b should contain a sufficient number of discrete photocells to achieve the desired resolution capability in detecting defects. For instance, with one arrangement for inspecting bearing balls having a given diameter between one-quarter inch and one-half inch, a linear solid state imager which is comprised of 256 discrete photocells could easily detect a defect having dimensions no greater than 3 mils (0.003 inches). The same resolution is achieved for inspecting bearing balls between one-half inch and one inch in diameter employing a linear solid state imager comprised or 512 photocells.

If an inspected bearing ball, such as bearing ball 202-d is found to have a defect, such as defect 224, accept-reject decision means 126 will be operated at a predetermined time after the inspection of that bearing ball has taken place, which predetermined time is sufficient for that bearing ball to roll to the left end of cylindrical tube 204. In response to the operation thereof, accept-reject decision means 126 controls the state of accept-reject track switch 214. Preferably, accept-rejection track switch 214 normally places track rails 200 in cooperative relationship with defect track rails 200d, and places track rails 200 in cooperative relationship with defect track rails 200c only if the inspected bearing ball has been found to have no defects. In a more sophisticated system than that shown in FIG. 2, defect track rails 200d will be further switched to any selected one of a plurality of track rail branches, depending upon the nature of each of a plurality of different types of defect characteristics that may be possessed by that defective bearing ball.

It has been found that the preferred embodiment of FIG. 2 is capable of accurately inspecting as many as 7 to 15 balls per second, spaced a ball diameter apart, the exact number depending upon the diameter of the inspected ball.

What is claimed is:

1. In a system for inspecting a bearing ball for the presence of a defect in the normally specularly-reflecting convex surface thereof; wherein said system comprises first means including a diffuser having an aperture therein for illuminating at least a portion of said convex surface with diffuse light, thereby to reflect a light-contrast pattern of a defect, if present, with respect to a diffuse-light background reflected from said normally specularly-reflecting portion of said surface, and second means, including light-imaging means positioned to be responsive to only that light reflected from said portion of said surface which has passed through said aperture, for detecting the presence of a defect-indicating light-contrast pattern; the improvement wherein:
   (a) said light-imaging means includes at least one one-dimensional imager positioned in cooperative relationship with said aperture to detect only a linear slice of said specularly-reflected light which has passed through said aperture, said linear slice being oriented substantially parallel to a first direction; and
   (b) said second means further includes third means for moving said bearing ball past said aperture by simultaneously rotating said bearing ball at a given angular velocity about an axis which is oriented in a second direction substantially perpendicular to said first direction while linearly translating said bearing ball at a certain translational velocity in a third direction which is oriented substantially perpendicular to both said first and second directions, and wherein said certain translational velocity has a value which is determined in accordance with a given function of the value of said given angular velocity that results in light specularly-reflected from substantially all points on an entire hemispheric surface of said bearing ball being detected by said one one-dimensional imager in response to said bearing ball, in passing by said aperture, rotating through a predetermined angle which is substantially less in value than 360°.

2. The system defined in claim 1, further comprising fourth means controlled by said second means for accepting an inspected bearing ball as non-defective only in response to said second means failing to detect the presence of a defect-indicating light contrast pattern reflected from that inspected bearing ball.

3. The system defined in claim 1, wherein:
   said one-dimensional imager is comprised of a linear-scanning video camera for deriving an output signal comprised of successively scanned image pixels.

4. The system defined in claim 3, wherein:
said second means includes an image processor responsive to the output signal image pixels from said video camera for processing said image pixels to determine whether or not a defect-indicating, light-contrast pattern exists on said bearing ball.

5. The system defined in claim 4, further comprising an analog-to-digital converter for converting said image pixels from analog-to-digital form, and wherein:
said image processor is a digital image processor controlled in accordance with a predetermined digital computer program.

6. The system defined in claim 4, further comprising fourth means controlled by said image processor for accepting an inspected bearing ball as non-defective only in response to a determination by said image processor that a defect-indicating, light-contrast pattern does not exist on said inspected bearing ball.

7. The system defined in claim 1, wherein:
said first means is comprised of a tube having a given cross-sectional dimensions and a longitudinal dimension extending between two opposite ends thereof, said tube being comprised of a wall of light-translucent material, whereby illumination of the exterior of said wall of said tube results in diffuse light being present substantially throughout the interior of said tube, said wall of said tube including at least one aperture therein for permitting that diffuse light specularly reflected from those points of the surface of a bearing ball situated within the interior of said tube that are in cooperative relationship with said one aperture to emerge from the interior to the exterior of said tube through said one aperture; and
said one-dimensional imager is situated external to said tube in cooperative relationship with said one aperture in said wall of said tube for receiving the specularly-reflected light emerging from the interior to the exterior of said tube through said one aperture in said wall of said tube.

8. The system defined in claim 7, wherein:
said one dimensional imager is comprised of a linear array camera.

9. The system defined in claim 7, wherein:
said second means includes a pair of track rails having a given portion thereof extending the length of the interior of said tube between said two opposite ends thereof, said pair of track rails being separated from one another by a selected distance $2r_x$ in which $r_x$ has a value with respect to the radius R of a bearing ball such that said bearing ball is supported at a certain distance $r_y$ below the center of said bearing ball; and
said second means further includes third means for rolling said bearing ball supported by said given portion of said track rails in a given longitudinal direction passed said one aperture at an angular velocity, whereby said supported bearing ball is translated at a linear velocity having a value that depends on the respective values of said angular velocity and said certain distance $r_y$.

10. The system defined in claim 9, wherein:
said angular velocity is a substantially constant angular velocity, whereby said linear velocity is a substantially constant linear velocity.

11. The system defined in claim 10, wherein:
said tube is in the form of an open-ended cylinder having its longitudinal axis oriented substantially horizontally;
said given portion of said track rails is oriented substantially horizontally; and
said track rails further includes a second portion thereof attached to one end of said given portion thereof that extends through one end of said open-ended cylinder to the exterior of said tube, said second portion of said track rails including a ramp rising vertically a given distance with respect to the level of said horizontal given portion of said track rails, whereby said bearing ball, if permitted to roll along said ramp, will achieve a predetermined constant angular velocity and a predetermined constant linear velocity upon reaching said horizontal given portion of said track rails.

12. The system defined in claim 11, further including a ball hopper for conveying a bearing ball to the top of said ramp so that a coveyed bearing ball can roll down said ramp.

13. The system defined in claim 12, wherein:
said ball hopper periodically conveys successive bearing balls to the top of said ramp at a predetermined rate, whereby successive bearing balls rolling on said given horizontal portion of said track rails are separated from one another by an amount that depends on said given linear velocity and said predetermined rate.

14. The system defined in claim 13, wherein:
said predetermined rate is such that successive bearing balls rolling on said given horizontal portion of said track rails are separated by substantially one diameter of a bearing ball.

15. The system defined in claim 11, wherein:
said bearing ball has a given diameter; and
said horizontal level of said given portion of said track along said given portion of said track rails is substantially coincident with the longitudinal axis of said cylinder.

16. The system defined in claim 15, wherein:
said light detection means includes a linear scanning video camera solid-state imager comprised of a periodically-scanned one-dimensional array of a predetermined number of photocells; and
said video camera is oriented with respect to said one aperture to scan a predetermined size arc of each successive latitude circumference of at least a portion of the surface of said bearing ball during the time said bearing ball rolls at constant angular and linear velocities passed said one aperture.

17. The system defined in claim 16, wherein:
said tube wall of said cylinder further includes another aperture therein for permitting that diffuse light specularly reflected from those points of the surface of said bearing ball that are in cooperative relationship with said other aperture to emerge from the interior to the exterior of said cylinder through said other aperture;
said light imaging means further comprises second light-detection means situated external to said cylinder in cooperative relationship with said other aperture for receiving the specularly-reflected light emerging from the interior to the exterior of said cylinder through said other aperture;
said second light detection means includes a second linear scanning video camera having a solid-state imager comprised of a periodically-scanned one-dimensional array of a predetermined number of photocells; and said second video camera is oriented with respect to said other aperture to scan a predetermined size arc of each successive latitude circumference of another portion of the surface of said bearing ball as said bearing ball rolls at constant angular and linear velocities passed said other aperture.

18. The system defined in claim 17, wherein:

said predetermined size arc that is scanned by each of said first and second video cameras is substantially 90°;

said one aperture and said first video camera are oriented so that a first of two opposite hemispheres of the surface of said ball bearing is scanned by said first video camera during the time said bearing ball rolls passed said one aperture; and said other aperture and said second video camera are oriented so that a second of said two opposite hemispheres of the surface of said bearing ball is scanned by said second video camera during the time said bearing ball rolls passed said other aperture.

19. The system defined in claim 16, wherein:

said second means includes fourth means coupled to said video camera for (1) detecting the presence of said bearing balls within the field-of-view of said video camera in response to the output signal intensity of said video camera, (2) initiating a timing cycle in response to the presence of said bearing ball being first detected, (3) counting the number of successive video camera scan periods following the initiation of said timing cycle, (4) initiating an inspection period only when said counted scan periods reaches a first predetermined number, said first predetermined number being less than one-half the number of scan periods required for a rolling bearing ball to traverse the field-of-view of said video camera whereby said initiation of said inspection period corresponds substantially to a selected latitude $-\theta_1$ of the surface of said rolling bearing ball then being in cooperative relationship with said one aperture, and (5) terminating said inspection period when said counted scan periods reaches a second predetermined number at which the termination of said inspection period corresponds substantially to a selected latitude $+\theta_1$ of the surface of said rolling bearing ball then being in cooperative relationship with said one aperture.

20. The system defined in claim 19, wherein:

$\theta_1$ has a value of less than 45°.

21. The system defined in claim 19, wherein:

the spacing distance $2r_x$ between said track rails is selected to provide a value for the distance $r_y$ that substantially conforms to the following equation, where R is the radius of a bearing ball:

$$r_y = R[180°/(180° - \theta_1)][\sin \theta_1/\pi]$$

22. The system defined in claim 21, wherein:

$\theta_1$ is no greater than 36°.

23. The system defined in claim 22, wherein:

$\theta_1$ is substantially 30°.

24. The system defined in claim 16, wherein said video camera's inability to directly receive retroreflected light when the zero degree latitude of said rolling bearing ball surface is in cooperative relationship with said one aperture results in a blind spot on said bearing ball surface that is not imaged by said video camera, and wherein:

said light-imaging means further includes auxiliary means for imaging said blind spot.

25. The system defined in claim 24, wherein:

said auxiliary means includes a half-mirror situated exterior to said cylinder in cooperative relationship with said one aperture, said half-mirror being oriented at a substantially 45° angle with respect to the detection of said retroreflected light, and illuminating means oriented at substantially 90° with respect to the direction of said retroreflected light for illuminating said half-mirror thereby to illuminate said blind spot with incident light reflected from said half-mirror that is substantially oppositely directed and parallel to said retroreflected light.

26. The system defined in claim 24, wherein:

said auxiliary means includes an auxiliary aperture in the wall of said cylinder that is longitudinally displaced from said one aperture and is so positioned that said blind spot on said rolling bearing ball surface comes into cooperative relationship with said auxiliary aperture at a different time from when said blind spot comes into cooperative relationship with said one aperture; and said auxiliary means further includes auxiliary light detection means situated exterior to said cylinder in cooperative relationship with said auxiliary aperture for receiving reflected light from said blind spot through said auxiliary aperture.

* * * * *